(12) United States Patent
Tanigawa et al.

(10) Patent No.: US 12,285,296 B2
(45) Date of Patent: Apr. 29, 2025

(54) ULTRASONIC DIAGNOSTIC APPARATUS, ULTRASONIC DIAGNOSTIC SYSTEM, AND METHOD FOR USE WITH THE ULTRASONIC DIAGNOSTIC APPARATUS

(71) Applicant: GE Precision Healthcare LLC, Wauwatosa, WI (US)

(72) Inventors: Shunichiro Tanigawa, Tokyo (JP); Naohisa Kamiyama, Tokyo (JP)

(73) Assignee: GE Precision Healthcare LLC, Wauwatosa, WI (US)

( * ) Notice: Subject to any disclaimer, the term of this patent is extended or adjusted under 35 U.S.C. 154(b) by 589 days.

(21) Appl. No.: 17/666,171

(22) Filed: Feb. 7, 2022

(65) Prior Publication Data
US 2022/0249066 A1 Aug. 11, 2022

(30) Foreign Application Priority Data
Feb. 10, 2021 (JP) ................. 2021-019622

(51) Int. Cl.
*A61B 8/00* (2006.01)
*A61B 8/08* (2006.01)
*G01S 7/52* (2006.01)

(52) U.S. Cl.
CPC ............... *A61B 8/54* (2013.01); *A61B 8/485* (2013.01); *A61B 8/488* (2013.01); *A61B 8/5207* (2013.01); *G01S 7/52042* (2013.01); *A61B 8/461* (2013.01)

(58) Field of Classification Search
CPC ........... A61B 8/54; A61B 8/485; A61B 8/488; A61B 8/5207; A61B 8/461; A61B 8/44;
(Continued)

(56) References Cited

U.S. PATENT DOCUMENTS 11,439,367 B2 * 9/2022 Sandrin .................. A61B 8/085
11,457,895 B2 * 10/2022 Audiere ................. A61B 8/085
(Continued)

FOREIGN PATENT DOCUMENTS

CN  114173672 A  *  3/2022
JP  64981832 A     4/2017

OTHER PUBLICATIONS

Sugimoto et al., "Clinical utilization of shear wave dispersion imaging in diffuse liver disease", Jan. 2020 (Year: 2020).*
(Continued)

*Primary Examiner* — Adil Partap S Virk

(57) ABSTRACT

Various ultrasonic diagnostic apparatuses and method are provided for calculating a velocity of propagation of shear waves. In one example, a method includes applying mechanical vibrations to a patient to generate shear waves, receiving first echo signals based on first ultrasonic pulses transmitted at a first pulse repetition frequency, creating data for an image based on the first echo signals, and calculating at least one frequency component of the mechanical vibrations. The method includes calculating a second pulse repetition frequency that is different from the first pulse repetition frequency, based on the at least one frequency component of the mechanical vibrations. The method include receiving second echo signals based on second ultrasonic pulses transmitted at the second pulse repetition frequency and calculating a velocity of propagation of said shear waves based on the second echo signals transmitted at the second pulse repetition frequency.

16 Claims, 7 Drawing Sheets

(58) Field of Classification Search
CPC ....... A61B 8/463; A61B 8/48; G01S 7/52042; G01S 7/5202
See application file for complete search history.

(56) References Cited

U.S. PATENT DOCUMENTS

| | | | | |
|---|---|---|---|---|
| 2002/0095087 | A1* | 7/2002 | Mourad | A61B 8/0816 600/442 |
| 2005/0165306 | A1* | 7/2005 | Zheng | A61B 8/485 600/437 |
| 2007/0038095 | A1* | 2/2007 | Greenleaf | A61B 8/485 600/438 |
| 2008/0249408 | A1* | 10/2008 | Palmeri | A61B 8/485 600/438 |
| 2009/0264754 | A1* | 10/2009 | Dahl | A61B 8/0875 600/438 |
| 2010/0069751 | A1* | 3/2010 | Hazard | A61B 8/00 600/438 |
| 2010/0222678 | A1* | 9/2010 | Bercoff | G06T 7/0012 600/442 |
| 2011/0063950 | A1* | 3/2011 | Greenleaf | G01S 7/52038 367/87 |
| 2012/0271166 | A1* | 10/2012 | Shao | A61B 8/5207 600/438 |
| 2013/0123630 | A1* | 5/2013 | Freiburger | A61B 8/485 600/443 |
| 2014/0296709 | A1* | 10/2014 | Fatemi | G16H 50/30 600/438 |
| 2015/0320394 | A1* | 11/2015 | Arnal | A61B 8/485 600/438 |
| 2018/0125455 | A1* | 5/2018 | Salcudean | A61B 8/485 |
| 2018/0256922 | A1* | 9/2018 | Mittelstein | A61N 7/00 |
| 2018/0271577 | A1* | 9/2018 | Bharat | A61B 34/10 |

OTHER PUBLICATIONS

CN114173672 Translation (Year: 2022).*
Turo et al., "Ultrasonic Characterization of the Upper Trapezius Muscle in Patients with Chronic Neck Pain", 2013 (Year: 2013).*
Oshiro et al., "Measurement of Rigidity and Viscosity Rate Using MRE," J-Stage Top, Medical Imaging Technology, vol. 19 (2001) No. 5, DOI https://doi.org/10.11409/mit.19.389, 11 pages.
Sugimoto et al., "Clinical utilization of shear wave dispersion imaging in diffuse liver disease," Ultrasonography 2020; 39(1): 3-10, https://doi.org/10.14366/usg.19031, 8 pages.

* cited by examiner

ULTRASONIC DIAGNOSTIC APPARATUS, ULTRASONIC DIAGNOSTIC SYSTEM, AND METHOD FOR USE WITH THE ULTRASONIC DIAGNOSTIC APPARATUS

FIELD

The present invention relates to an ultrasonic diagnostic apparatus and an ultrasonic diagnostic system for calculating the velocity of propagation of shear waves, and a program for controlling the ultrasonic diagnostic apparatus.

BACKGROUND

Techniques for quantifying the properties of a patient's tissue include one that detects shear waves generated in the inside of the patient to calculate a parameter relating to the tissue properties. For example, Japanese Patent Application KOKAI No. 2019-118820 discloses an ultrasonic apparatus for generating shear waves in the inside of a patient by an ultrasonic push pulse, and calculating a quantitative value of viscosity based on the frequency and velocity of propagation of the shear waves.

In generating shear waves in the inside of a patient's liver, for example, by an ultrasonic push pulse, such shear waves are very faint, and have a short propagation distance and a poor S/N ratio. Under such bad conditions, it is difficult to detect the shear waves and calculate a parameter relating to tissue properties. It is desired to more reliably calculate a parameter relating to tissue properties.

BRIEF SUMMARY

This summary introduces concepts that are described in more detail in the detailed description. It should not be used to identify essential features of the claimed subject matter, nor to limit the scope of the claimed subject matter.

An ultrasonic diagnostic apparatus or an ultrasonic diagnostic system in one mode has solved the aforementioned problem by generating shear waves by applying mechanical vibrations, in place of a push pulse, to a patient. Ultrasonic pulses for detecting shear waves need to be transmitted at a pulse repetition frequency corresponding to a frequency component in mechanical vibrations. Accordingly, the ultrasonic diagnostic apparatus or ultrasonic diagnostic system in the one mode creates data for an image representing propagation of shear waves based on echo signals from the ultrasonic pulses transmitted at a first pulse repetition frequency. A pulse repetition frequency is then determined based on the image. More specifically, the ultrasonic diagnostic apparatus or ultrasonic diagnostic system in the one mode comprises an ultrasonic probe for transmitting ultrasonic pulses and receiving echo signals to/from a patient, and a processor. The processor controls said ultrasonic probe to transmit said ultrasonic pulses at at least one first pulse repetition frequency to a patient, to said patient mechanical vibrations containing at least one frequency component having been applied to generate shear waves of a frequency according to said at least one frequency component, and creates data for an image representing propagation of said shear waves based on the echo signals from the ultrasonic pulses transmitted at said first pulse repetition frequency. Moreover, the processor calculates at least one velocity of propagation of said shear waves based on echo signals from ultrasonic pulses transmitted at a pulse repetition frequency determined based on said image.

According to the ultrasonic diagnostic apparatus in the mode described above, the velocity of propagation of shear waves is calculated based on echo signals obtained by ultrasonic pulses transmitted at a pulse repetition frequency determined based on an image representing propagation of shear waves generated by mechanical vibrations. By using mechanical vibrations in place of a push pulse, the velocity of propagation of shear waves can be more reliably obtained. Moreover, a more suitable pulse repetition frequency for detecting shear waves can be obtained based on the aforementioned image.

DETAILED DESCRIPTION

Figure 1:
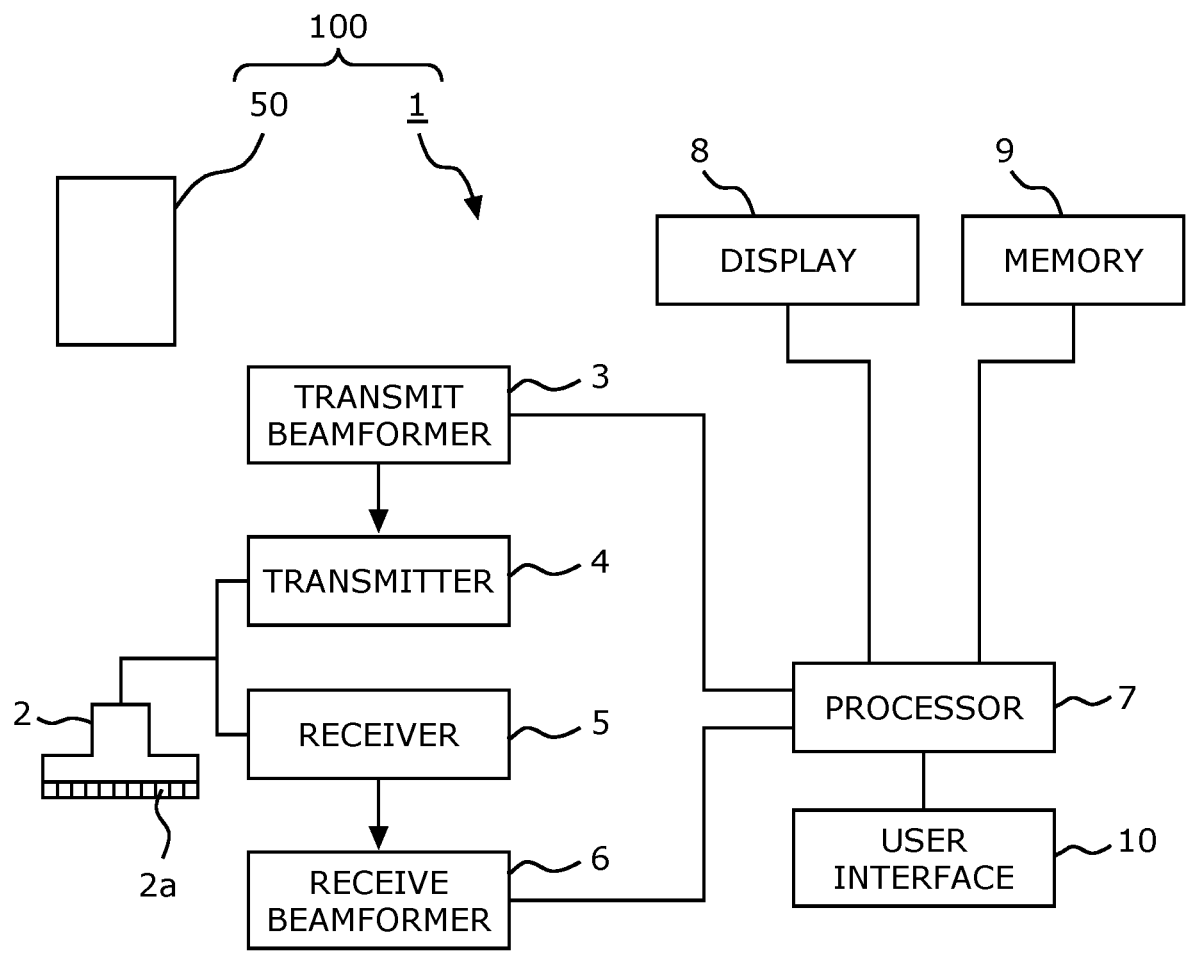
FIG. 1 is a block diagram showing an example of an ultrasonic diagnostic system and an ultrasonic diagnostic apparatus in accordance with an embodiment.

Now embodiments of the present invention will be described hereinbelow with reference to the accompanying drawings. An ultrasonic diagnostic system 100 shown in FIG. 1 comprises an ultrasonic diagnostic apparatus 1 and a vibrator 50. The ultrasonic diagnostic apparatus 1 comprises an ultrasonic probe 2, a transmit beamformer 3, and a transmitter 4. The ultrasonic probe 2 performs an ultrasonic scan on a patient, and receives ultrasonic echoes.

More specifically, the ultrasonic probe 2 has a plurality of vibration elements 2a for emitting pulsed ultrasound to a patient (not shown). The plurality of vibration elements 2a are driven by the transmit beamformer 3 and transmitter 4 to emit pulsed ultrasound. The vibration elements 2a are piezoelectric elements.

The ultrasonic diagnostic apparatus 1 further comprises a receiver 5 and a receive beamformer 6. The pulsed ultrasound emitted from the vibration elements 2a is reflected in the inside of the patient to generate echoes returning to the vibration elements 2a. The echoes are converted into electrical signals by the vibration elements 2a, which are echo signals, and are input to the receiver 5. The echo signals undergo amplification, etc. with a required gain at the receiver 5, and then input to the receive beamformer 6, where receive beamforming is performed. The receive beamformer 6 outputs receive-beamformed ultrasound data.

The receive beamformer 6 may be a hardware beamformer or a software beamformer. In the case that the receive beamformer 6 is a software beamformer, it may comprise one or more processors including one or more of a graphics processing unit (GPU), a microprocessor, a central processing unit (CPU), a digital signal processor (DSP), or other kinds of processors capable of executing logical operations. The processor(s) constituting the receive beamformer 6 may be constructed from a processor separate from a processor 7 described later, or constructed from the processor 7.

The ultrasonic probe 2 may comprise electrical circuitry to perform all or part of transmit and/or receive beamforming. For example, all or part of the transmit beamformer 3, transmitter 4, receiver 5, and receive beamformer 6 may be situated within the ultrasonic probe 2.

The ultrasonic diagnostic apparatus 1 also comprises the processor 7 for controlling the transmit beamformer 3, transmitter 4, receiver 5, and receive beamformer 6. Moreover, the ultrasonic diagnostic apparatus 1 comprises a display 8, memory 9, and a user interface 10.

The processor 7 comprises one or more processors. The processor 7 is in electronic communication with the ultrasonic probe 2. The processor 7 may control the ultrasonic probe 2 to acquire ultrasound data. The processor 7 controls which of the vibration elements 2a are active, and the shape of an ultrasonic beam transmitted from the ultrasonic probe 2. The processor 7 is also in electronic communication with the display 8, and the processor 7 may process the ultrasound data into ultrasonic images for display on the display 8. The term "electronic communication" may be defined to include both wired and wireless connections. The processor 7 may include a central processing unit (CPU) according to one embodiment. According to other embodiments, the processor 7 may include other electronic components capable of carrying out processing functions, such as a digital signal processor, a field-programmable gate array (FPGA), a graphics processing unit (GPU), or any other type of processor. According to other embodiments, the processor 7 may include a plurality of electronic components capable of carrying out processing functions. For example, the processor 7 may include two or more electronic components selected from a list of electronic components including: a central processing unit, a digital signal processor, a field-programmable gate array, and a graphics processing unit.

The processor 7 may also include a complex demodulator (not shown) that demodulates RF data. In another embodiment, the demodulation can be carried out earlier in the processing chain.

The processor 7 is adapted to perform one or more processing operations according to a plurality of selectable ultrasonic modalities on the data. The data may be processed in real-time during a scanning session as the echo signals are received. For the purpose of this disclosure, the term "real-time" is defined to include a procedure that is performed without any intentional delay.

The data may be temporarily stored in a buffer (not shown) during ultrasonic scanning, so that they can be processed in a live operation or in an off-line operation not in real-time. In this disclosure, the term "data" may be used to refer to one or more datasets acquired using the ultrasonic diagnostic apparatus 1.

The ultrasound data may be processed by the processor 7 in other or different mode-related modules (e.g., B-mode, color Doppler, M-mode, color M-mode, spectral Doppler, contrast-enhanced mode, elastography, TVI, strain, strain rate, and the like) to form data for ultrasonic images. For example, one or more modules may produce ultrasonic images in B-mode, color Doppler, M-mode, color M-mode, spectral Doppler, contrast-enhanced mode, elastography, TVI, strain, strain rate, and combinations thereof, and the like.

The image beams and/or image frames are stored and timing information indicating a time at which the data was acquired in memory may be recorded. The modules may include, for example, a scan conversion module to perform scan conversion operations to convert the image frames from coordinate beam space to display space coordinates. A video processor module may be provided that reads the image frames from memory and displays the image frames in real-time while a procedure is being carried out on the patient. The video processor module may store the image frames in image memory, from which the ultrasonic images are read and displayed on the display 8.

As used herein, the term "image" may broadly refer to both a visible image, and data representing a visible image. The term "data" may include both raw data that is ultrasound data before the scan conversion operations, and image data that is data after the scan conversion operations.

In the case that the processor 7 includes a plurality of processors, the aforementioned processing tasks to be handled by the processor 7 may be handled by the plurality of processors. For example, a first processor may be utilized to demodulate and decimate the RF signal while a second processor may be used to further process the data prior to displaying an image.

In the case that the receive beamformer 6 is a software beamformer, for example, its processing functions may be carried out by a single processor or by a plurality of processors.

The display 8 is an LED (Light Emitting Diode) display, an LCD (Liquid Crystal Display), an organic EL (Electro-Luminescence) display, or the like.

The memory 9 is any known data storage medium. In an example, the ultrasonic image display system 1 comprises non-transitory storage media and transitory storage media as the memory 9, and comprises a plurality of units of memory 9. The non-transitory storage medium is, for example, a non-volatile storage medium such as an HDD (Hard Disk Drive) and ROM (Read Only Memory). The non-transitory storage media may include a portable storage medium such as a CD (Compact Disc) and a DVD (Digital Versatile Disc). In the non-transitory storage medium, programs executed by the processor 7 are stored.

The transitory storage medium is a volatile storage medium such as RAM (Random Access Memory).

The user interface 10 can accept an operator's input. For example, the user interface 10 accepts an input of a command and/or information from the operator. The user interface 10 is constructed to include a keyboard, hard keys, a trackball, a rotary control, soft keys, and the like. The user interface 10 may include a touch screen that displays soft keys, etc.

The vibrator 50 generates mechanical vibrations. In an example, the vibrator 50 comprises piezoelectric elements, to which drive voltage is applied to generate mechanical vibrations. The mechanical vibrations contain at least a first frequency component f1 and a second frequency component f2.

The vibrator 50 operates independently of the ultrasonic diagnostic apparatus 1, and it has its own power source.

Figure 2:
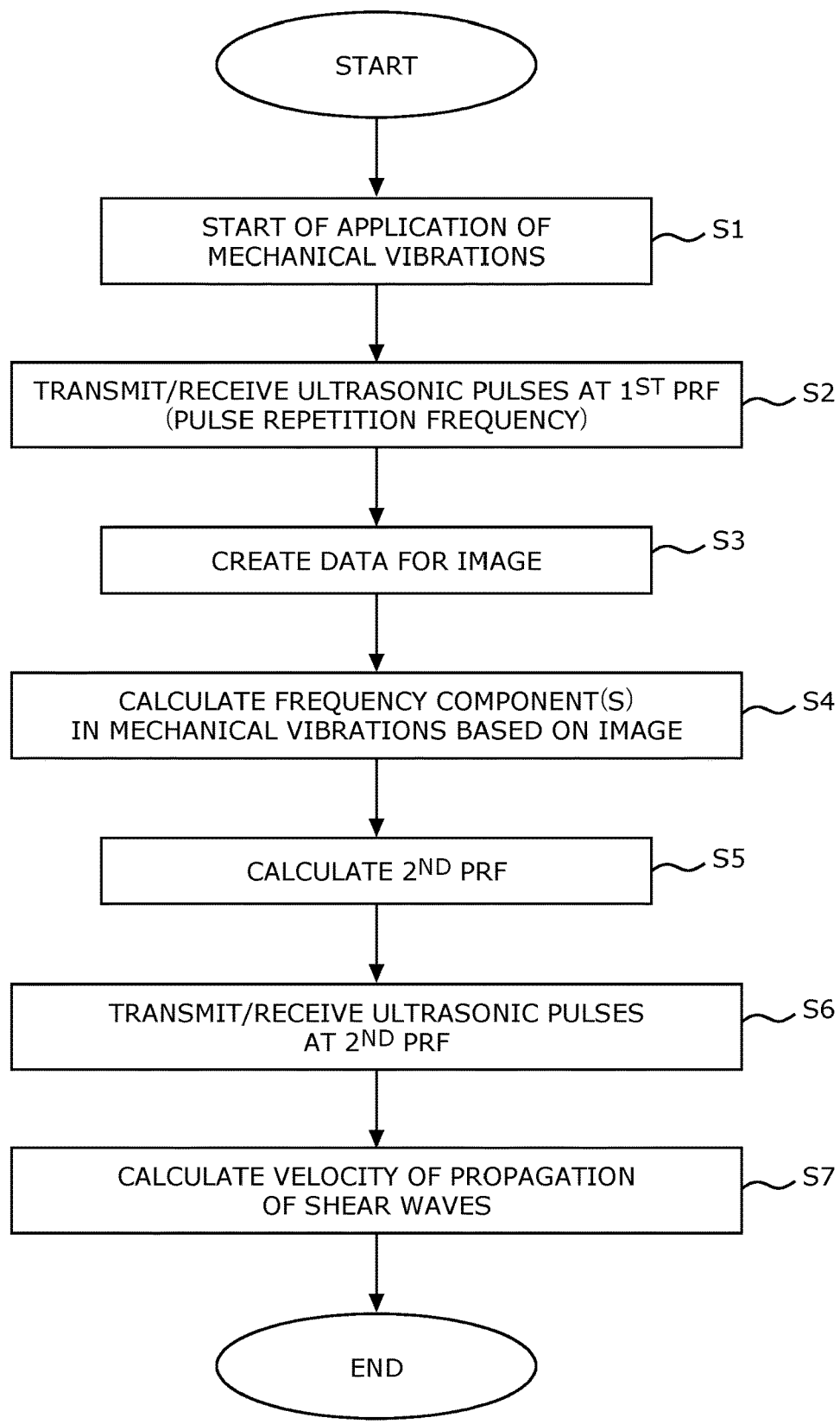
FIG. 2 is an example of a flow chart showing processing in the embodiment.

Next, processing in the present embodiment will be described. FIG. 2 is a flow chart showing processing in the present embodiment. First, at Step S1, the vibrator 50 starts application of mechanical vibrations to the patient. The vibrator 50 applies mechanical vibrations while it is put on a surface of the patient. In an example, an operator puts the vibrator 50 on the surface of the patient, and activates the vibrator 50. The mechanical vibrations induce shear waves in biological tissue in the inside of the patient.

Next, at Step S2, for the patient in which shear waves are generated by mechanical vibrations, the processor 7 controls the ultrasonic probe 2 to transmit/receive ultrasonic pulses at a first pulse repetition frequency PRF1 for a required period of time. Although the first pulse repetition frequency PRF1 is a frequency that enables detection of shear waves and calculation of a velocity of propagation of the shear waves, a second pulse repetition frequency PRF2, which will be discussed later, enables more reliable and accurate calculation of the velocity of propagation of shear waves.

Next, at Step S3, the processor 7 creates data for an image representing propagation of shear waves based on echo signals from the ultrasonic pulses transmitted at Step S2. More specifically, the processor 7 performs tissue Doppler processing on the echo signals from the ultrasonic pulses transmitted at Step S2, and creates Doppler data. The processor 7 then creates data for an image representing propagation of shear waves based on the Doppler data. In an example, the data for an image representing propagation of shear waves is created by a technique described in Japanese Patent No. 6498183. The image representing propagation of shear waves renders shear waves forming a stripe pattern. The image may be a video image.

Next, at Step S4, the processor 7 calculates at least one frequency component in mechanical vibrations based on the data for an image created at Step S3. Since the data for an image created at Step S3 represents a periodic change in IQ signals obtained in tissue Doppler processing, the processor 7 calculates at least one frequency component in mechanical vibrations based, for example, on the IQ signal, the first pulse repetition frequency PRF1, and the frame rate in the ultrasonic pulse transmission/reception at Step S2.

Next, at Step S5, the processor 7 calculates a second pulse repetition frequency PRF2 for ultrasonic pulses according to the frequency component in mechanical vibrations calculated at Step S4. Now the second pulse repetition frequency PRF2 will be described in detail. As discussed earlier, shear waves are detected using a tissue Doppler technique of detecting tissue motion. In the tissue Doppler technique, a frequency of tissue motion, that is, a vibration frequency, has a corresponding pulse repetition frequency for ultrasonic pulses that enables more reliable and accurate detection of the motion. Therefore, the second pulse repetition frequency PRF2 is a frequency set according to the frequency component in mechanical vibrations calculated at Step S4 to facilitate more reliable detection of shear waves in tissue Doppler processing.

In an example, the relationship between the second pulse repetition frequency PRF2 and the frequency component in mechanical vibrations calculated at Step S4 may be that given by EQ. (1) described in Paragraph 0016 of Japanese Patent No. 6498183. Specifically, it may be:

$$f=\{(2m+1)/4\}*PRF2,$$

wherein f is the frequency component in mechanical vibrations calculated at Step S4, m is an integer equal to or greater than zero, and PRF2 is the second pulse repetition frequency PRF2. The equation above may be used to calculate the second pulse repetition frequency PRF2 for ultrasonic pulses according to the frequency component in mechanical vibrations. That is, $$PRF2=4*f/(2m+1).$$

Next, at Step S6, for the patient in which shear waves are generated by mechanical vibrations, the processor 7 controls the ultrasonic probe 2 to transmit/receive ultrasonic pulses at the second pulse repetition frequency PRF2 calculated at Step S5 for a required period of time.

Next, at Step S7, the processor 7 calculates a velocity of propagation of shear waves based on echo signals from the ultrasonic pulses transmitted at Step S6. The processor 7 performs tissue Doppler processing on echo signals from the ultrasonic pulses and creates Doppler data, based on which it calculates a velocity of propagation. The processor 7 may create data for an image representing propagation of shear waves based on the Doppler data. The processor 7 may also display an image based on the data for the image on the display 8.

By continuous mechanical vibrations applied to the patient as in the present embodiment, shear waves of greater amplitude can be generated as compared with a case in which an ultrasonic push pulse is used. Therefore, the velocity of propagation of shear waves can be calculated with more reliability as a parameter relating to properties of a patient's tissue. Since a frequency component in mechanical vibrations is calculated based on data for an image representing propagation of shear waves, a more suitable second pulse repetition frequency according to the frequency of shear waves can be obtained.

Figure 3:
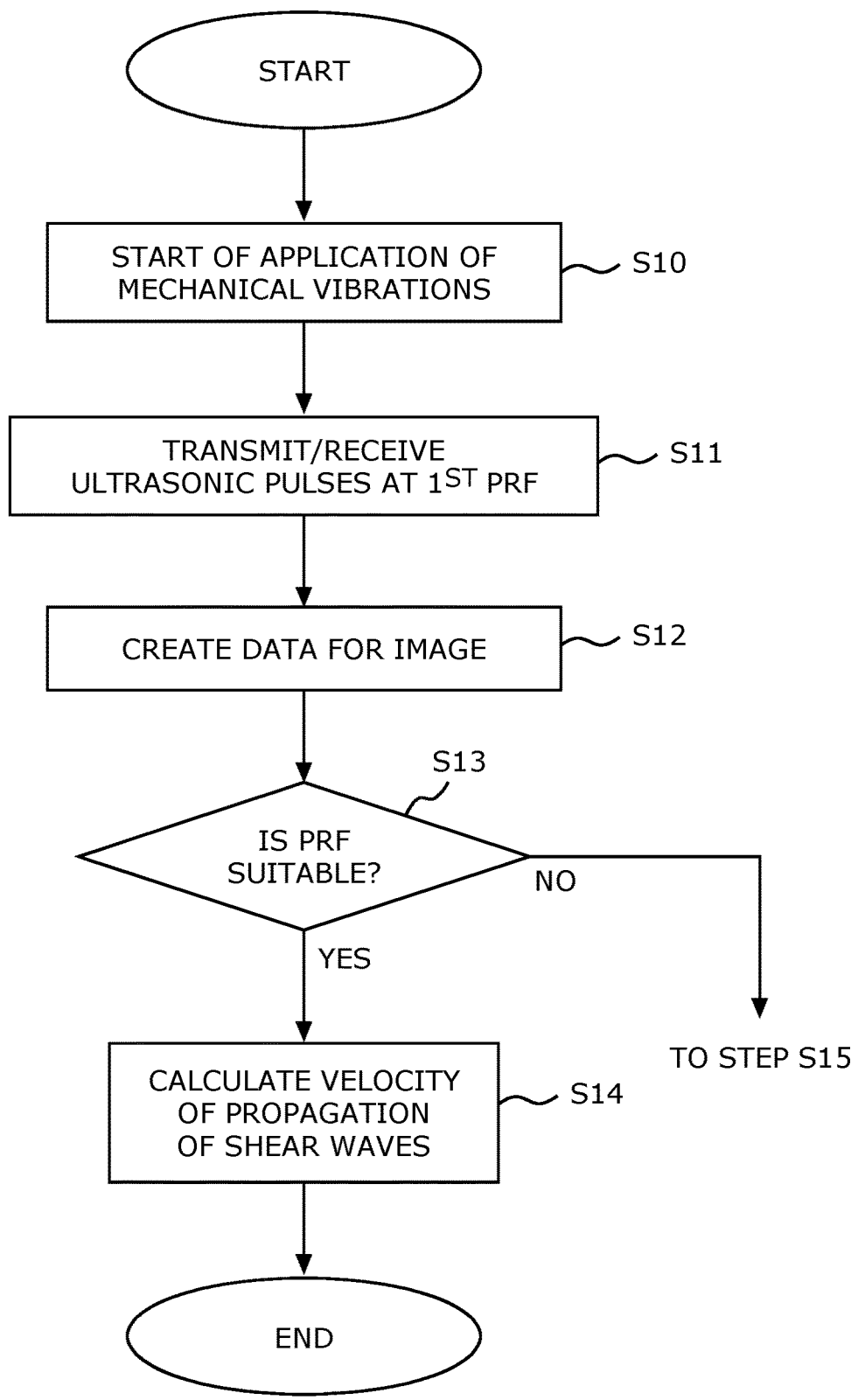
FIG. 3 is another example of a flow chart showing processing in the embodiment.
Figure 4:
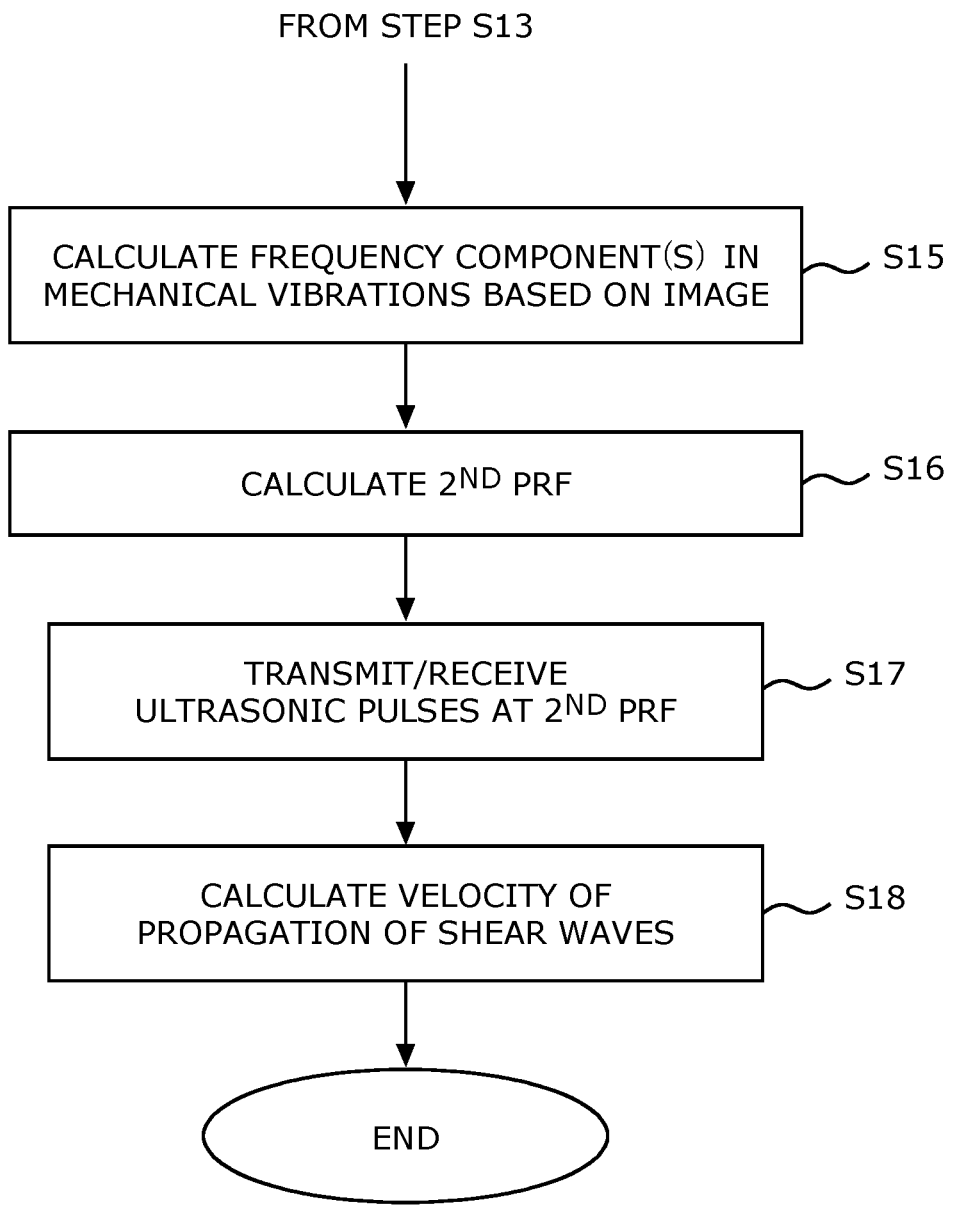
FIG. 4 is an example of a flow chart showing processing in the case that a first pulse repetition frequency is decided not to be suitable in the flow chart in FIG. 3.

Next, a variation of the embodiment will be described. To begin with, a first variation will be described. FIGS. 3 and 4 are flow charts showing processing of the first variation. Since the processing from Step S10 to Step S12 is identical to that from Step S1 to Step S3, explanation thereof will be omitted. In the present variation, however, the value of the first pulse repetition frequency PRF1 at Step S11 may be different from that at Step S2. At Step S13, whether the first pulse repetition frequency PRF1 is suitable or not is decided. In an example, the processor 7 decides whether the first pulse repetition frequency is suitable or not based on the data for an image obtained at Step S12.

The decision by the processor 7 will described in some more detail. When the pulse repetition frequency for ultrasonic pulses for detecting shear waves is a suitable frequency according to the frequency of shear waves, the direction of travel of shear waves displayed on an image representing propagation of shear waves is assumed to be a specific one. Accordingly, in an example, when the image obtained at Step S12 is a video image indicating that the direction of travel of shear waves is opposite to a proper direction of travel, the processor 7 decides that the first pulse repetition frequency PRF1 is not suitable. In other examples, the processor 7 may decide that the first pulse repetition frequency PRF1 is not suitable in the case that wavefronts of shear waves cannot be detected in the image obtained at Step S12, or that shear waves are propagating in a direction different from a distribution of biological tissue. It should be noted that the decision techniques provided here are merely illustrative.

The decision at Step S13 may be performed by the operator. In this case, the processor 7 displays an image on the display 8 based on the data for the image obtained at Step S12. The operator decides whether the first pulse repetition frequency PRF1 is suitable or not based on the displayed image. Similarly to the decision technique by the processor 7 described above, the operator may perform the decision based on the direction of travel of shear waves or detectability of wavefronts. The operator inputs whether the first pulse repetition frequency PRF1 is suitable or not at the user interface 10.

In the case that the processor 7 has decided that the first pulse repetition frequency PRF1 is suitable at Step S13 ("YES" at Step S13), the flow goes to processing at Step S14. Likewise, in the case that the user interface 10 has accepted an operator's input indicating that the first pulse repetition frequency PRF1 is suitable at Step S13 ("YES" at Step S13), the flow goes to processing at Step S14.

In the first variation, the first pulse repetition frequency PRF1 decided to be suitable may be said to be a frequency according to a frequency component in mechanical vibrations, i.e., a frequency that enables reliable and accurate calculation of the velocity of propagation of shear waves, similarly to the second pulse repetition frequency PRF2 calculated at Step S5 in FIG. 2.

At Step S14, the processor 7 calculates a velocity of propagation of shear waves based on the Doppler data created at Step S12. Upon completing the calculation of the velocity of propagation at Step S14, the processing is terminated.

On the other hand, in the case that the processor 7 decides that the first pulse repetition frequency PRF1 is not suitable ("NO" at Step S13), the flow goes to processing at Step S15. Likewise, in the case that the user interface 10 has accepted an operator's input indicating that the first pulse repetition frequency PRF1 is not suitable at Step S13 ("NO" at Step S13), the flow goes to processing at Step S15.

Figure 5:
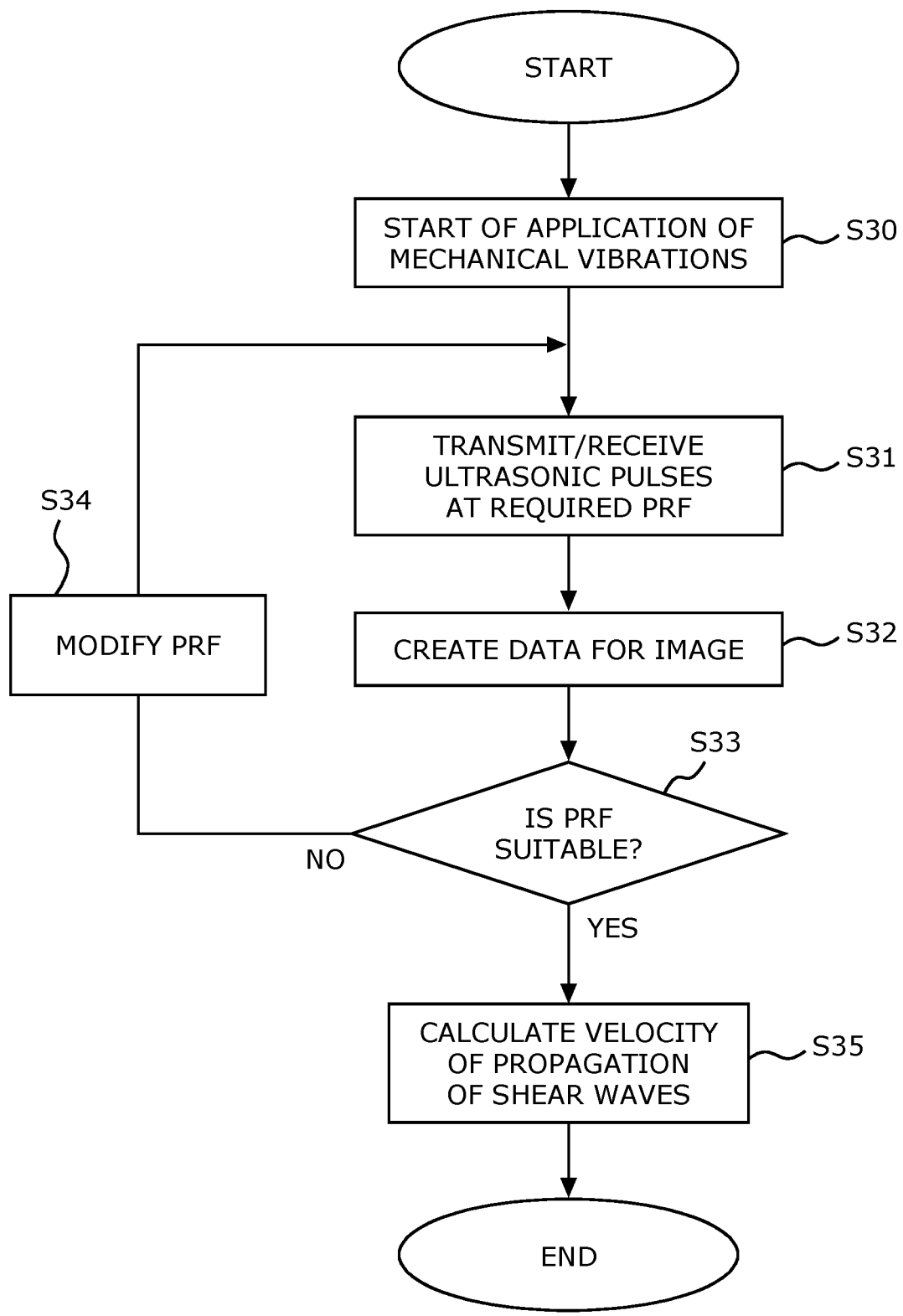
FIG. 5 is an example of a flow chart showing processing in a fourth variation of the embodiment.

The processing from Step S15 is shown in the flow chart in FIG. 4. The processing from Step S15 to Step S18 shown in FIG. 5 is similar to that at Steps S4 to Steps S7.

Next, a second variation will be described. Mechanical vibrations applied at Steps S1 and S10 described earlier may contain at least a first frequency component f1 and a second frequency component f2. Shear waves generated in biological tissue in the inside of the patient by the mechanical vibrations contain first shear waves of a frequency according to the first frequency component f1 and second shear waves of a frequency according to the second frequency component f2. The frequency of the first shear waves and that of the second shear waves are different from each other.

The first pulse repetition frequency PRF1 at Steps S2 and S11 may contain two first pulse repetition frequencies PRF11 and PRF12. More specifically, the processor 7 modifies the first pulse repetition frequency PRF1 during Steps S2 and S11. The processor 7 modifies the first pulse repetition frequency PRF1 after a required period of time has passed since ultrasonic pulse transmission/reception was started at Steps S2 and S11. The first pulse repetition frequency PRF1 before modification will be referred to as a first pulse repetition frequency PRF11, and the first pulse repetition frequency PRF1 before modification will be referred to as a first pulse repetition frequency PRF12 hereinbelow. Therefore, at Steps S2 and S11, ultrasound transmission/reception is performed with the first pulse repetition frequency PRF11 for a required period of time, and then, with the first pulse repetition frequency PRF12 for a required period of time.

At Steps S3 and S12, the processor 7 creates Doppler data based on echo signals from the ultrasonic pulses transmitted/received at the first pulse repetition frequency PRF11, and based on the Doppler data, it creates data for a first image representing propagation of first shear waves. The processor 7 also creates Doppler data based on echo signals from the ultrasonic pulses transmitted/received at the first pulse repetition frequency PRF12, and based on the Doppler data, it creates data for a second image representing propagation of second shear waves.

At Step S13, whether the first pulse repetition frequency PRF11 is a suitable frequency according to the first shear waves or not is decided based on the data for a first image. Moreover, at Step S13, whether the first pulse repetition frequency PRF12 is a suitable frequency according to the second shear waves or not is decided based on the data for a second image.

At Steps S4 and S15, the processor 7 calculates a first frequency component f1 in mechanical vibrations based on the data for a first image. The calculation technique is basically identical to that explained for Step S4 described earlier, except that the processor 7 calculates the first frequency component f1 using the first pulse repetition frequency PRF11 in place of the first pulse repetition frequency PRF1 described earlier.

At Steps S4 and S15, the processor 7 also calculates a second frequency component f2 in mechanical vibrations based on the data for a second image. The calculation technique is basically identical to that explained for Step S4 described earlier, except that the processor 7 calculates the second frequency component f2 using the first pulse repetition frequency PRF12 in place of the first pulse repetition frequency PRF1 described earlier.

At Steps S5 and S16, the processor 7 calculates two second pulse repetition frequencies PRF21 and PRF22 as the second pulse repetition frequency PRF2. The second pulse repetition frequency PRF21 is a pulse repetition frequency according to the first frequency component f1. The second pulse repetition frequency PRF22 is a pulse repetition frequency according to the second frequency component f2.

At Steps S6 and S17, ultrasonic pulse transmission/reception is performed with the second pulse repetition frequency PRF21 for a required period of time, and then, with the second pulse repetition frequency PRF22 for a required period of time.

At Steps S7 and S18, the processor 7 creates Doppler data based on echo signals from the ultrasonic pulses transmitted at the second pulse repetition frequency PRF21, and calculates a velocity V1 of propagation of the first shear waves. The processor 7 also creates Doppler data based on echo signals from the ultrasonic pulses transmitted at the second pulse repetition frequency PRF22, and calculates a velocity V2 of propagation of the second shear waves.

At Step S14, the processor 7 calculates a velocity V1 of propagation of the first shear waves based on Doppler data created based on echo signals from the ultrasonic pulses transmitted at the first pulse repetition frequency PRF11. The processor 7 also calculates a velocity V2 of propagation of the second shear waves based on Doppler data created based on echo signals from the ultrasonic pulses transmitted at the first pulse repetition frequency PRF12.

In the second variation, the processor 7 may calculate a parameter relating to properties of a patient's tissue using the first and second velocities V1, V2 of propagation. Now an example of calculation of the parameter will be described hereinbelow.

The velocity of propagation of shear waves changes with the frequency of shear waves. Specifically, the higher the frequency of shear waves is, the higher the velocity of propagation of shear waves is. Moreover, depending upon viscosity of a medium through which shear waves propagate, the degree of change of the velocity of propagation against the frequency, that is, a slope in the distribution of the frequency and the velocity of propagation changes. Accordingly, the processor 7 uses the first and second velocities V1, V2 of propagation and the first and second frequency components f1, f2 as parameters to calculate a viscosity-related value. Since the frequency of shear waves depends upon the frequency of mechanical vibrations, the first and second frequency components f1, f2 are used here in calculation of the viscosity-related value. In an example, the viscosity-related value is a slope in the distribution of the frequency components f1, f2 and velocities V1, V2 of propagation, i.e., (V2−V1)/(f2−f1). The processor 7 may also calculate a coefficient of viscosity based on the slope.

Next, a third variation will be described. In the third variation, similarly to the second variation, mechanical vibrations applied at Steps S1 and S10 described earlier contain at least a first frequency component f1 and a second frequency component f2, and first shear waves and second shear waves are generated.

However, unlike the second variation, the number of the first pulse repetition frequencies PRF1 at Steps S2 and S11 is one. Therefore, data for an image representing propagation of shear waves is created at Steps S3 and S12.

At Step S13, whether the first pulse repetition frequency PRF1 is a suitable frequency according to first shear waves and second shear waves or not is decided based on the data for an image created at Step S12.

At Steps S4 and S15, based on the data for an image, the processor 7 calculates a first frequency component f1 in mechanical vibrations. Moreover, at Steps S4 and S15, based on the data for an image, the processor 7 calculates a second frequency component f2 in mechanical vibrations.

At Steps S5 and S16, the processor 7 calculates a second pulse repetition frequency PRF2. However, the processor 7 calculates the second pulse repetition frequency PRF2 according to both the first frequency component f1 and second frequency component f2. In an example, the second pulse repetition frequency PRF2 is a common multiple of the first and second frequency components f1, f2. The common multiple may be the least common multiple.

Alternatively, the pulse repetition frequency PRF2 may be the one satisfying two equations derived from EQ. (1) described in Paragraph 0016 of Japanese Patent No. 6498183 mentioned above, as given below:

$$PRF2=4*f1(2m+1), \text{ and}$$

$$PRF2=4*f2(2n+1)$$

wherein m and n are integers equal to or greater than zero, and PRF2 is the pulse repetition frequency PRF2.

At Steps S7 and S18, the processor 7 creates Doppler data based on echo signals from the ultrasonic pulses transmitted at the second pulse repetition frequency PRF2 at Steps S6 and 517, and calculates velocities V1, V2 of propagation of the first and second shear waves.

At Step S14, velocities V1, V2 of propagation of the first and second shear waves are calculated based on the Doppler data created at Step S12.

In the third variation, similarly to the second variation, a viscosity-related value may be calculated using the first and second velocities V1, V2 of propagation.

Next, a fourth variation will be described. FIG. 5 is a flow chart showing processing in the fourth variation. The processing at Step S30 is identical to that at Steps S1 and S10. Next, at Step S31, the processor 7 controls the ultrasonic probe 2 to transmit/receive ultrasonic pulses at a required pulse repetition frequency for a required period of time. The processor 7 initially sets a first pulse repetition frequency PRF1 as the required pulse repetition frequency, as in Step S11.

At Step S32, the processor 7 creates data for an image representing propagation of shear waves in a similar manner to Steps S3 and S12.

At Step S33, whether the required pulse repetition frequency set at Step S31 is suitable or not is decided based on the data for an image created at Step S32 or on the image, in a similar manner to Step S13. In the case that the first pulse repetition frequency PRF1 is set at Step S31, whether the first pulse repetition frequency PRF1 is suitable or not is decided at Step S33.

In the case that the first pulse repetition frequency PRF1 is decided not to be suitable at Step S33 ("NO" at Step S33), the flow goes to processing at Step S34. On the other hand, in the case that the first pulse repetition frequency PRF1 is decided to be suitable at Step S33 ("YES" at Step S13), the flow goes to processing at Step S35. At Step S35, the processor 7 calculates a velocity of propagation of shear waves based on the Doppler data crated at Step S32.

At Step S34, the processor 7 modifies the first pulse repetition frequency PRF1 into a third pulse repetition frequency PRF3. In an example, the third pulse repetition frequency PRF3 has a value obtained by incrementing or decrementing the value of the first pulse repetition frequency PRF1 by a prespecified frequency Act. The pulse repetition frequency after being modified from the initially set first pulse repetition frequency PRF1 will be referred to herein as the third pulse repetition frequency PRF3.

Once the third pulse repetition frequency PRF3 has been set at Step S34, the processor 7 controls the ultrasonic probe 2 to transmit/receive ultrasonic pulses at the third pulse repetition frequency PRF3 for a required period of time at Step S31. Then, at Step S32, data for an image is created based on echo signals from the ultrasonic pulses transmitted/received at the third pulse repetition frequency PRF3, whereupon whether the third pulse repetition frequency PRF3 is suitable or not is decided at Step S33. In the case that the third pulse repetition frequency PRF3 is decided not to be suitable, the prespecified frequency Act is added or subtracted again to set a new third pulse repetition frequency PRF3 at Step S34, and the processing at Step S31 and thereafter is performed.

On the other hand, in the case that the third pulse repetition frequency PRF3 is decided to be suitable at Step S33 ("YES" at Step S33), the flow goes to processing Step S35, where a velocity of propagation of shear waves is calculated based on the Doppler data created at Step S32 immediately before. The third pulse repetition frequency PRF3 decided to be suitable at Step S33 may be regarded as the second pulse repetition frequency PRF2.

While the present invention has been described with reference to particular embodiments, various changes may be made and/or equivalents may be substituted without departing from the scope and spirit of the present invention. In addition, many modifications may be made to adapt a particular situation or material to the teachings of the invention, without departing from the scope and spirit of the present invention. Therefore, the present invention is not limited to the particular embodiments disclosed herein, and it is intended that the present invention will encompass all the embodiments falling within the appended claims.

For example, the vibrator 50 may be connected with the ultrasonic diagnostic apparatus 1. In this case, the vibrator 50 may be supplied with electric power from the ultrasonic diagnostic apparatus 1.

Figure 6:
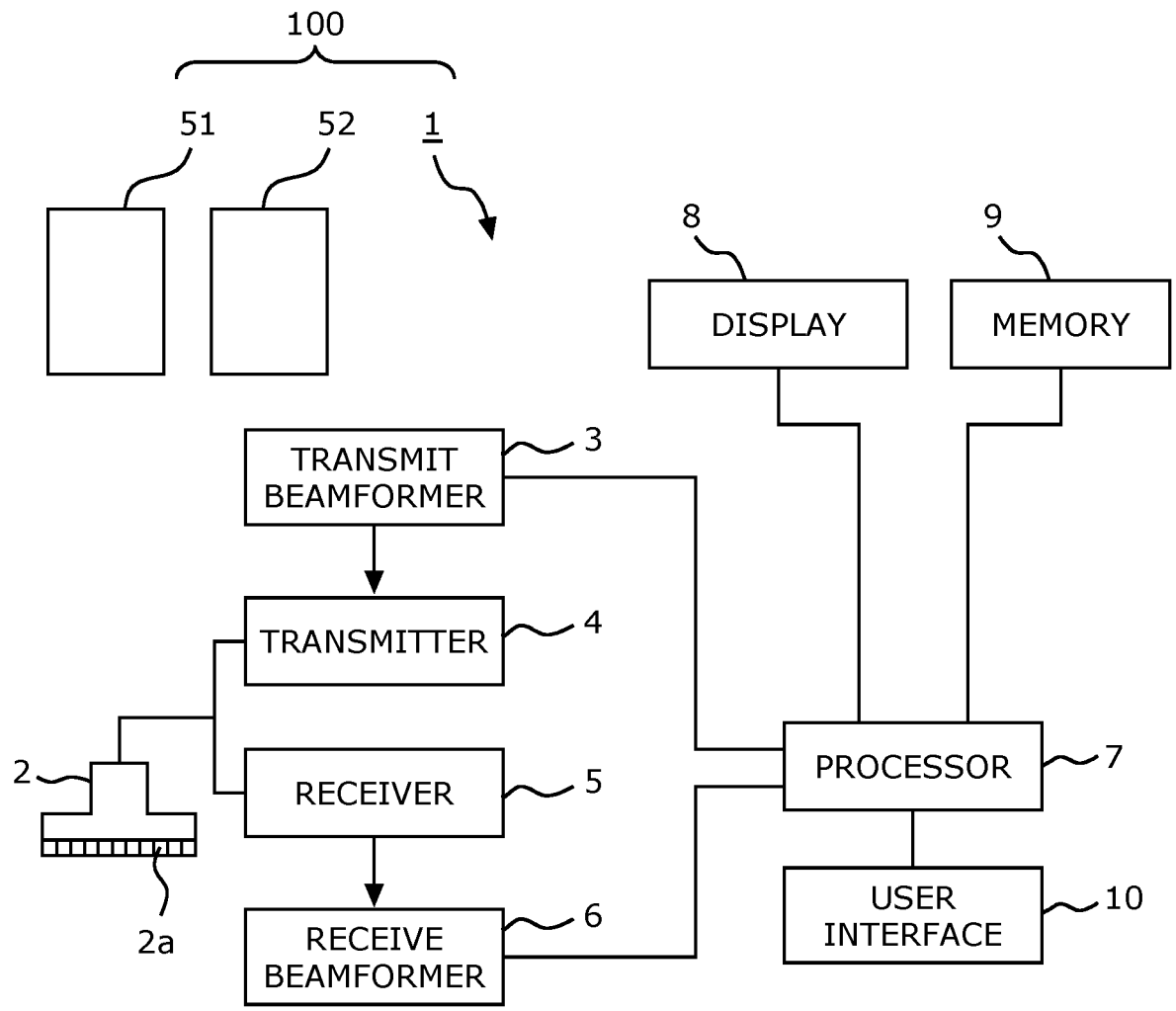
FIG. 6 is a block diagram showing an example of the ultrasonic diagnostic system and ultrasonic diagnostic apparatus in another embodiment.

Moreover, the ultrasonic diagnostic system 100 may comprise a first vibrator 51 and a second vibrator 52, in place of the vibrator 50, as shown in FIG. 6. Although the basic configurations of the first vibrator 51 and second vibrator 52 are identical to that of the vibrator 50, the first vibrator 51 generates mechanical vibrations of a first frequency component f1 while the second vibrator 52 generates mechanical vibrations of a second frequency component f2.

Furthermore, in the first variation, the first pulse repetition frequency PRF1 may be set according to the frequency component in mechanical vibrations. In this case, the first pulse repetition frequency PRF1 is a frequency that enables reliable and accurate calculation of the velocity of propagation of shear waves. However, the frequency component in mechanical vibrations may change due to vibrator degradation with time, etc. In this case, the first pulse repetition frequency set according to the frequency component in mechanical vibrations before the change needs to be set again according to the change of the frequency component. Thus, the decision at Step S13 in FIG. 3 may be made based on whether or not re-setting of the first pulse repetition frequency PRF1 is required. More specifically, at Step S13, the processor 7 calculates a frequency component in mechanical vibrations based on the data for an image created at Step S12, in a similar manner to Step S4. Next, the processor 7 compares the calculated frequency component in mechanical vibrations with the frequency component in mechanical vibrations before the change corresponding to the first pulse repetition frequency PRF1. The frequency component in mechanical vibrations before the change is known. Next, in the case that a difference between the frequency components being compared exceeds a required range, the processor 7 decides that the first pulse repetition frequency PRF1 is not suitable. On the other hand, in the case that the difference between the frequency components being compared falls within the required range, the processor 7 decides that the first pulse repetition frequency PRF1 is suitable.

The processor 7 may output a warning when the first pulse repetition frequency PRF1 is not suitable. The warning may be displayed on the display 8 or output from a speaker (omitted in the drawings) of the ultrasonic diagnostic apparatus 1.

In the case that the first pulse repetition frequency PRF1 is decided not to be suitable, the flow goes to processing at Step S18 and thereafter, without executing the processing at Step S17 in FIG. 5. Thus, ultrasound transmission/reception is performed with the second pulse repetition frequency PRF2, in place of the first pulse repetition frequency PRF1. The second pulse repetition frequency PRF2 is a frequency according to a frequency component in mechanical vibrations after the change.

Likewise, the decision at Step S13 in the second variation may be made based on whether or not re-setting of the first pulse repetition frequencies PRF11 and PRF12 is required.

Figure 7:
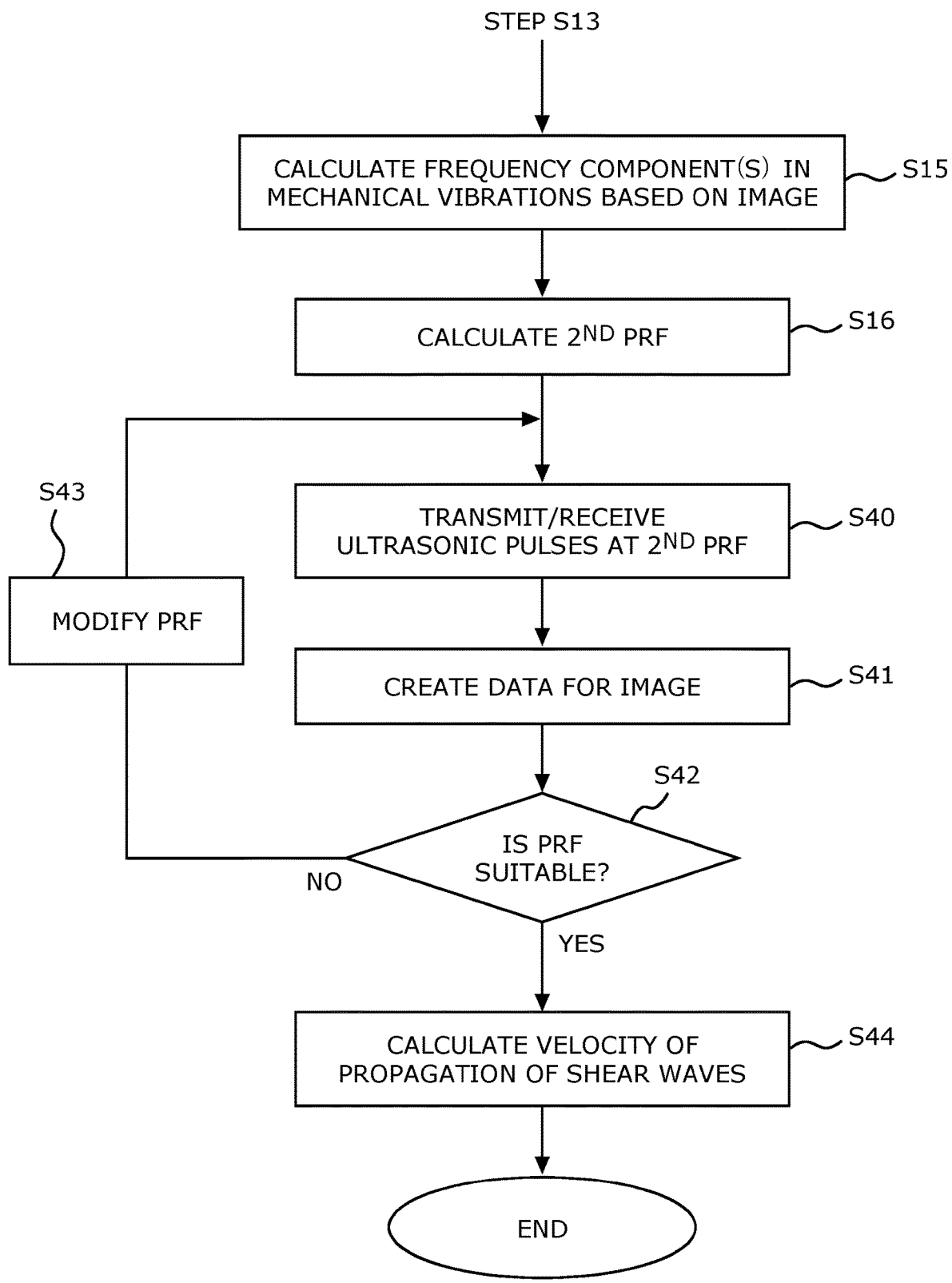
FIG. 7 is another example of a flow chart showing processing in the case that the first pulse repetition frequency is decided not to be suitable in the flow chart in FIG. 3.

Moreover, in the first variation, whether the second pulse repetition frequency PRF2 calculated at Step S16 is suitable or not may be decided. The processing in this case will now be described with reference to the flow chart in FIG. 7. Once the second pulse repetition frequency PRF2 has been calculated at Step S16, the flow goes to processing at Step S40. At Step S40, the processor 7 controls the ultrasonic probe 2 to transmit/receive ultrasonic pulses at the second pulse repetition frequency PRF2 for a required period of time, as in Steps S6 and S17.

Next, at Step S41, the processor 7 creates data for an image representing propagation of shear waves based on echo signals from the ultrasonic pulses transmitted at Step S40, in a similar manner to Steps S3, S12 and S32. Next, at Step S42, whether the second pulse repetition frequency PRF2 is suitable or not is decided based on the data for an image created at Step S41 or on the image, in a similar manner to Step S13.

In the case that the second pulse repetition frequency PRF2 is decided not to be suitable at Step S42 ("NO" at Step S42), the flow goes to processing at Step S43. On the other hand, in the case that the second pulse repetition frequency PRF2 is decided to be suitable at Step S42 ("YES" at Step S42), the flow goes to processing at Step S44. At Step S44, the processor 7 calculates a velocity of propagation of shear waves based on the Doppler data created at Step S41.

At Step S43, the processor 7 modifies the second pulse repetition frequency PRF2. In an example, the modified second pulse repetition frequency PRF2 has a value obtained by incrementing or decrementing the value of the second pulse repetition frequency PRF2 before modification by a prespecified frequency Aa.

Once the second pulse repetition frequency PRF2 has been modified at Step S43, the flow goes back to the processing at Step S40. At Step S40, ultrasonic pulses are transmitted/received at the modified second pulse repetition frequency PRF2, and the processing thereafter is executed.

In addition, the embodiments described above may be a method of controlling an ultrasonic diagnostic apparatus, said apparatus comprising: an ultrasonic probe for transmitting ultrasonic pulses and receiving echo signals to/from a patient; and a processor, said method comprising the steps of:
controlling, by said processor, said ultrasonic probe to transmit said ultrasonic pulses at at least one first pulse repetition frequency to a patient, to said patient mechanical vibrations containing at least one frequency component having been applied to generate shear waves of a frequency according to said at least one frequency component;
creating, by said processor, data for an image representing propagation of said shear waves based on the echo signals from said ultrasonic pulses transmitted at said first pulse repetition frequency; and
calculating, by said processor, at least one velocity of propagation of said shear waves based on echo signals from ultrasonic pulses transmitted at a pulse repetition frequency determined based on said image.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

The invention claimed is:
1. An ultrasonic diagnostic apparatus comprising:
an ultrasonic probe; and
a processor, said processor being adapted to:
control said ultrasonic probe to transmit first ultrasonic pulses at a first pulse repetition frequency to a patient and to receive first echo signals from the patient, wherein a vibrator provides first mechanical vibra- tions to the patient during the process of transmitting the first ultrasonic pulses and receiving the first echo signals;

create data for an image based on the first echo signals from said first ultrasonic pulses transmitted at said first pulse repetition frequency;

calculate, based on said data for the image, at least one frequency component of said first mechanical vibrations applied to the patient to generate first shear waves;

calculate a second pulse repetition frequency, different from the first pulse repetition frequency, based on the at least one frequency component of the first mechanical vibrations;

control the ultrasonic probe to transmit second ultrasonic pulses at the second pulse repetition frequency to the patient and to receive second echo signals from the patient, wherein the vibrator provides second mechanical vibrations to the patient during the process of transmitting the second ultrasonic pluses and receiving the second echo signals, wherein the second mechanical vibrations and the first mechanical vibrations share the at least one frequency component;

calculate at least one velocity of propagation of second shear waves based on the second echo signals from the second ultrasonic pulses transmitted at the second pulse repetition frequency.

2. The ultrasonic diagnostic apparatus as recited in claim 1, wherein the processor is further adapted to determine that the first pulse repetition frequency does not propagate suitable first shear waves based on the data for the image before calculating said second pulse repetition frequency, wherein the suitability of the first shear waves is determined based on one or more of a travel direction the first shear waves and a detectability of the first shear waves in the image.

3. The ultrasonic diagnostic apparatus as recited in claim 2, wherein said processor makes said decision based on said data for the image, and when deciding that said first pulse repetition frequency does not propagate the suitable first shear waves, said processor controls said ultrasonic probe to transmit said second ultrasonic pulses at said second pulse repetition frequency.

4. The ultrasonic diagnostic apparatus as recited in claim 2, comprising:

a display; and a user interface for accepting an operator's input, wherein said processor displays said image based on the data for said image on said display, and once said user interface has accepted said operator's input deciding that said first pulse repetition frequency does not propagate the suitable first shear waves based on said image, said processor controls said ultrasonic probe to transmit said ultrasonic pulses at said second pulse repetition frequency in place of said first pulse repetition frequency.

5. The ultrasonic diagnostic apparatus as recited in claim 1, comprising:

a display; and a user interface for accepting an operator's input, wherein:

said processor:

displays said image on said display, and once said user interface has accepted said operator's input deciding that said first pulse repetition frequency does not propagate suitable first shear waves based on said image, said processor automatically transmits said second ultrasonic pulses at the second pulse repetition frequency wherein the suitability of the first shear waves is determined based on one or more of a travel direction the first shear waves and a detectability of the first shear waves in the image.

6. The ultrasonic diagnostic apparatus as recited in claim 1, wherein:

said processor performs tissue Doppler processing on the second echo signals from said second ultrasonic pulses transmitted at said second pulse repetition frequency to create Doppler data, and creates said data for an image representing propagation of said shear waves based on said Doppler data.

7. The ultrasonic diagnostic apparatus as recited in claim 1, wherein said first and second mechanical vibrations contain at least a first frequency component and a second frequency component of the at least one frequency component.

8. The ultrasonic diagnostic apparatus as recited in claim 1, wherein:

said first and second mechanical vibrations contain at least a first frequency component and a second frequency component of the at least one frequency component, said first shear waves contain a frequency according to said first frequency component and said second shear waves contain a frequency according to said second frequency component, said at least one velocity of propagation contains a first velocity of propagation of said first shear waves and a second velocity of propagation of said second shear waves, said velocities being calculated based on the echo signals from said ultrasonic pulses transmitted at respective pulse repetition frequencies determined based on said image, and said processor further uses said first velocity of propagation and said second velocity of propagation to calculate a parameter relating to tissue properties for said patient.

9. An ultrasonic diagnostic system comprising:

an ultrasonic probe;

a processor; and a vibrator for applying mechanical vibrations containing at least one frequency component to said patient, wherein said processor is adapted to:

control said ultrasonic probe to transmit first ultrasonic pulses at a first pulse repetition frequency to a patient and to receive first echo signals from the patient, wherein the vibrator provides first mechanical vibrations to the patient during the process of transmitting the first ultrasonic pulses and receiving the first echo signals;

create data for an image based on the first echo signals from said first ultrasonic pulses transmitted at said first pulse repetition frequency;

calculate, based on said data for the image, at least one frequency component of said first mechanical vibrations applied to the patient to generate first shear waves;

calculate a second pulse repetition frequency, different from the first pulse repetition frequency, based on the at least one frequency component of the first mechanical vibrations;

control the ultrasonic probe to transmit second ultrasonic pulses at the second pulse repetition frequency to the patient and to receive second echo signals from the patient, wherein the vibrator provides second mechanical vibrations to the patient during the process of transmitting the second ultrasonic pluses and receiving the second echo signals, wherein the second mechanical vibrations and the first mechanical vibrations share the at least one frequency component;

calculate at least one velocity of propagation of second shear waves based on the second echo signals from the second ultrasonic pulses transmitted at the second pulse repetition frequency.

10. The ultrasonic diagnostic system as recited in claim 9, wherein:

said vibrator is constructed to comprise at least a first vibration source and a second vibration source, said first vibration source applies mechanical vibrations of a first frequency component of the at least one frequency component, and said second vibration source applies mechanical vibrations of a second frequency component of the at least one frequency component.

11. A method for use with an ultrasonic diagnostic apparatus including an ultrasonic probe and a processor, the method comprising:

applying mechanical vibrations to a patient with a vibrator to generate shear waves;

controlling, with the processor, the ultrasonic probe to transmit first ultrasonic pulses at a first pulse repetition frequency to a patient and to receive first echo signals from the patient while the mechanical vibrations are being applied to the patient;

creating, with the processor, data for an image based on the first echo signals from the first ultrasonic pulses transmitted at the first pulse repetition frequency;

calculating, with the processor, at least one frequency component of the mechanical vibrations applied to the patient based on the data from the image;

calculating, with the processor, a second pulse repetition frequency, different from the first pulse repetition frequency, based on the at least one frequency component of the mechanical vibrations;

controlling the ultrasonic probe to transmit second ultrasonic pulses at the second pulse repetition frequency to the patient and to receive second echo signals from the patient while the mechanical vibrations are being applied to the patient; and calculating, with the processor, at least one velocity of propagation of second shear waves based on the second echo signals from the second ultrasonic pulses transmitted at the second pulse repetition frequency.

12. The method of claim 11, further comprising determining that the first pulse repetition frequency does not propagate suitable first shear waves based on the data for the image, wherein the suitability of the first shear waves is determined based on one or more of a travel direction the first shear waves and a detectability of the first shear waves in the image.

13. The method of claim 12, wherein said calculating the second pulse repetition frequency is performed automatically by the processor in response to determining that the first pulse repetition frequency does not propagate the suitable first shear waves.

14. The method of claim 12, wherein the at least one frequency component of the mechanical vibrations comprises a first frequency component and a second frequency component different than the first frequency component.

15. The method of claim 11, wherein said determining that the first pulse repetition frequency is not suitable is performed manually by an operator, and wherein said calculating the second pulse frequency is performed by the processor in response to an input from the operator indicating that the first pulse repetition frequency does not propagate suitable first shear waves.

16. The method of claim 11, wherein the second pulse repetition frequency is determined by the processor according to the following equation:

$$PRF2 = 4*f/(2m+1)$$

wherein PRF2 is the second pulse repetition frequency, f is the at least one frequency component of the mechanical vibrations, and m is an integer equal to or greater than zero.

* * * * *